(12) United States Patent
Mori

(10) Patent No.: US 8,039,654 B2
(45) Date of Patent: Oct. 18, 2011

(54) ESTERIFICATION REACTION PRODUCT, GELLING AGENT CONTAINING THE PRODUCT, AND COSMETIC PREPARATION CONTAINING THEM

(75) Inventor: Haruki Mori, Kanagawa (JP)

(73) Assignee: The Nisshin Oillio Group, Ltd., Tokyo (JP)

( * ) Notice: Subject to any disclaimer, the term of this patent is extended or adjusted under 35 U.S.C. 154(b) by 444 days.

(21) Appl. No.: 12/309,687

(22) PCT Filed: Jul. 20, 2007

(86) PCT No.: PCT/JP2007/064319
§ 371 (c)(1),
(2), (4) Date: Jan. 27, 2009

(87) PCT Pub. No.: WO2008/013106
PCT Pub. Date: Jan. 31, 2008

(65) Prior Publication Data
US 2009/0324519 A1     Dec. 31, 2009

(30) Foreign Application Priority Data

Jul. 28, 2006  (JP) ................................. 2006-206806
Oct. 12, 2006  (JP) ................................. 2006-278686

(51) Int. Cl.
*A23D 9/00* (2006.01)
(52) U.S. Cl. ............ 554/224; 554/227; 424/59; 424/63; 424/64; 424/70.12; 510/122; 510/158; 514/772.3; 528/295.5
(58) Field of Classification Search ............ 424/59, 424/63, 64, 70.12; 554/224, 227; 510/122, 510/158; 514/772.3; 528/295.5
See application file for complete search history.

(56) References Cited

U.S. PATENT DOCUMENTS
5,436,006 A    7/1995   Hirose et al.

FOREIGN PATENT DOCUMENTS
| JP | 56-104807 | 8/1981 |
| JP | 06-093288 | 4/1994 |
| JP | 09-104613 | 4/1997 |
| JP | 2001-247846 | 9/2001 |
| JP | 2003-238988 | 8/2003 |

OTHER PUBLICATIONS

Form PCT/IB/338.
Form PCT/IB/373.
English-Language Translation of Form PCT/ISA/237, 2009.

*Primary Examiner* — Deborah D Carr
(74) *Attorney, Agent, or Firm* — McGinn IP Law Group, PLLC

(57) ABSTRACT

Disclosed is an esterification reaction product which is capable of gelling both an oil agent and a cyclic silicone or a volatile dimethylpolysiloxane, or both an oil agent and a nonvolatile dimethylpolysiloxane. Also disclosed are a gelling agent contacting the esterification reaction product, and a cosmetic preparation containing the esterification reaction product or the gelling product and having an excellent feeling of use. Specifically, the cosmetic preparation contains, as a gelling agent, an esterification reaction product which is obtained by esterifying a component A that is a polyhydric alcohol or a condensate thereof, a component B that is a saturated dibasic acid having 10-28 carbon atoms, a component C that is a linear saturated fatty acid having 16-28 carbon atoms, and a component D that is a branched saturated fatty acid having 8-28 carbon atoms at a blending ratio (component A:component B) of 1.0 mole:0.10-0.20 mole.

20 Claims, No Drawings

ESTERIFICATION REACTION PRODUCT, GELLING AGENT CONTAINING THE PRODUCT, AND COSMETIC PREPARATION CONTAINING THEM

TECHNICAL FIELD

The present invention relates to an esterification reaction product, a gelling agent containing the product, and a cosmetic preparation containing them. In particular, the invention relates to an esterification reaction product which is capable of gelating both an oil agent and a cyclic silicone or a volatile dimethylpolysiloxane, or both an oil agent and a non-volatile dimethylpolysiloxane, a gelling agent containing the product, and a cosmetic preparation containing the product or the agent and having an excellent feeling of use.

BACKGROUND ART

The formulation form of a cosmetic preparation may be multifarious ranging from liquid preparations to solid preparations, and formulation forms requiring gelation or solidification make use of gelling agents or the like.

As conventionally used gelling agents, there are known glyceryl behenate/eicosanedioate, 12-hydroxystearic acid, dextrin fatty acid esters, sucrose fatty acid esters, inulin fatty acid esters, acylated cellobiose, dibenzylidene monosorbitol (DBMSA), amino acid-based gelling agents, fatty acid metal salts, silicic anhydride, organically modified clay minerals, fumed silica, alumina, crosslinked organopolysiloxanes, and the like.

Meanwhile, in regard to cosmetic preparations, various silicone compounds such as cyclic silicones, volatile dimethylpolysiloxanes and non-volatile dimethylpolysiloxanes, or oil agents such as alcohols and ester oil agents, is used as a purpose of improving feeling of use and the like.

In regard also to the cosmetic preparations having such silicone compounds such as cyclic silicones, volatile dimethylpolysiloxanes and non-volatile dimethylpolysiloxanes or oil agents such as alcohols and ester oil agents incorporated therein, formulation forms requiring gelation or solidification similarly make use of gelling agents.

As for the gelling agents for silicone compounds such as cyclic silicones, volatile dimethylpolysiloxanes and non-volatile dimethylpolysiloxanes, inulin fatty acid esters have been developed (see, for example, Patent Document 1). Furthermore, as for the gelling agents for alcohols, ester oil agents and the like, esterification products of glycerin or the like with linear saturated fatty acids having 2 to 28 carbon atoms and aliphatic saturated dibasic acids having 12 to 28 carbon atoms, have been developed (see, for example, Patent Documents 2 and 3).

Patent Document 1: JP-A No. 2004-300094
Patent Document 2: JP-A No. 7-126603
Patent Document 3: JP-A No. 7-126604

DISCLOSURE OF THE INVENTION

Problems to be Solved by the Invention

However, in regard to the inulin fatty acid esters, the esters can gelate a wide variety of silicone compounds, but for the oil agents, there is a limitation to the oil agents that can gelate. On the other hand, in regard to the esterification products of glycerin or the like with a linear saturated fatty acid having 2 to 28 carbon atoms and an aliphatic saturated dibasic acid having 12 to 28 carbon atoms, the products can gelate a wide variety of oil agents, but for the silicone compounds, the esterification products can gelate only a small portion of silicone compounds used for cosmetic uses, such as methylphenylpolysiloxanes. Thus, the esterification products could not gelate cyclic silicones and volatile dimethylpolysiloxanes that are generally used in cosmetic preparation or the like, and had poor solubility in the cyclic silicones and volatile dimethylpolysiloxanes under heating. Furthermore, the esterification products of glycerin or the like with a linear saturated fatty acid having 2 to 28 carbon atoms and an aliphatic saturated dibasic acid having 12 to 28 carbon atoms could not gelate non-volatile dimethylpolysiloxanes as well, and had poor solubility in the non-volatile dimethylpolysiloxanes under heating.

Therefore, it is an object of the present invention to provide an esterification reaction product which is capable of gelating both a cyclic silicone and an oil agent, or both a volatile dimethylpolysiloxane and an oil agent, and a gelling agent containing the product. It is another object of the present invention to provide an esterification reaction product which is capable of gelating both a non-volatile dimethylpolysiloxane and an oil agent, and a gelling agent containing the product.

Furthermore, it is another object of the present invention to provide a cosmetic preparation containing the esterification reaction product or the gelling agent and having an excellent feeling of use.

Means for Solving the Problems

The present intention provides, in order to achieve the objects, an esterification reaction product having a hydroxyl value of 30 or less, which is obtainable by subjecting the following component A, component B, component C and component D to esterification reaction, characterized in that the blending ratio of the component A and component B at the time of the esterification reaction is such that component A:component B=1.0 mole:0.10 to 0.20 moles:

Component A: a polyhydric alcohol or a condensate thereof,

Component B: a saturated dibasic acid having 10 to 28 carbon atoms,

Component C: a linear saturated fatty acid having 16 to 28 carbon atoms, and

Component D: a branched saturated fatty acid having 8 to 28 carbon atoms.

Furthermore, the present invention also provides, in order to achieve the objects, a gelling agent characterized by containing the esterification reaction product according to the present invention.

The present invention provides, in order to achieve the objects, a cosmetic preparation containing the esterification reaction product according to the present invention or the gelling agent according to the present invention.

Effects of the Invention

According to the present invention, an esterification reaction product capable of gelating both a cyclic silicone and an oil agent, or both a volatile dimethylpolysiloxane and an oil agent, and a gelling agent containing the product can be provided. Furthermore, an esterification reaction product capable of gelating both a non-volatile dimethylpolysiloxane and an oil agent, and a gelling agent containing the product can be provided.

In addition, according to the present invention, a cosmetic preparation containing the esterification reaction product or the gelling agent, and having excellent feeling of use, can be provided.

BEST MODE FOR CARRYING OUT THE INVENTION

[Esterification Reaction Product According to Embodiments of Present Invention]

The esterification reaction product according to an embodiment of the present invention is an esterification reaction product having a hydroxyl value of 30 or less, which is obtainable by subjecting the following component A, component B, component C and component D to esterification reaction, characterized in that the blending ratio of the component A and component B at the time of the esterification reaction is such that component A:component B=1.0 mole: 0.10 to 0.20 moles:

Component A: a polyhydric alcohol or a condensate thereof,

Component B: a saturated dibasic acid having 10 to 28 carbon atoms,

Component C: a linear saturated fatty acid having 16 to 28 carbon atoms, and

Component D: a branched saturated fatty acid having 8 to 28 carbon atoms.

According to the present embodiment, the esterification reaction may mean both esterification and oligoesterification resulting in a straight-chained or network-shaped structure.

(Component A: Polyhydric Alcohol or Condensate Thereof)

As the polyhydric alcohol of component A, such an alcohol having 3 to 30 carbon atoms is preferred, one having 3 to 6 carbon atoms is more preferred, and one having 3 to 5 carbon atoms is particularly preferred. When the number of carbon atoms of the polyhydric alcohol is within the above range, the gelation ability for the cyclic silicone or volatile dimethylpolysiloxane and the oil agent is favorable.

Specific examples of the polyhydric alcohol include glycerin, trimethylolpropane and pentaerythritol, and in particular, glycerin and trimethylolpropane are preferred in terms of the gelation ability for the cyclic silicone or volatile dimethylpolysiloxane and the oil agent.

As for the polyhydric alcohol condensate of component A, the polyhydric alcohol is as described previously, and the degree of polymerization of the condensate is preferably 1 to 10, more preferably 1 to 4, and particularly preferably 1 or 2. When the degree of polymerization of the polyhydric alcohol condensate is within the range described above, the gelation ability for the cyclic silicone or volatile dimethylpolysiloxane and the oil agent is favorable.

Specific examples of the polyhydric alcohol condensate include polyglycerins such as diglycerin, triglycerin, tetraglycerin and decaglycerin, ditrimethylolpropane, dipentaerythritol and the like, and in particular, diglycerin is preferred in terms of the gelation ability for the cyclic silicone or volatile dimethylpolysiloxane and the oil agent.

(Component B: Saturated Dibasic Acid Having 10 to 28 Carbon Atoms)

As for the saturated dibasic acid of component B, such an acid having 10 to 28 carbon atoms is preferred, one having 16 to 24 carbon atoms is more preferred, and one having 18 or 20 carbon atoms is particularly preferred. When the number of carbon atoms of the saturated dibasic acid is within the range described above, the gelation ability for the cyclic silicone or volatile dimethylpolysiloxane and the oil agent is favorable.

Specific examples of the saturated dibasic acid include eicosanedioic acid, octadecanedioic acid, sebacic acid and the like, and in particular, eicosanedioic acid is preferred in terms of the gelation ability for the cyclic silicone or volatile dimethylpolysiloxane and the oil agent.

(Component C: Linear Saturated Fatty Acid Having 16 to 28 Carbon Atoms)

As for the linear saturated fatty acid of component C, such a fatty acid having 16 to 28 carbon atoms is preferred, one having 16 to 24 carbon atoms is more preferred, and one having 18 to 22 carbon atoms is particularly preferred. When the number of carbon atoms of the linear saturated fatty acid is within the range described above, the gelation ability for the cyclic silicone or volatile dimethylpolysiloxane and the oil agent is favorable.

Specific examples of the linear saturated fatty acid include palmitic acid, stearic acid, eicosanoic acid, behenic acid, montanic acid, lignoceric acid and the like, and in particular, palmitic acid, stearic acid or behenic acid, inter alia, behenic acid, is preferred in terms of the gelation ability for the cyclic silicone or volatile dimethylpolysiloxane and the oil agent.

(Component D: Branched Saturated Fatty Acid Having 8 to 28 Carbon Atoms)

As for the branched saturated fatty acid of component D, such a fatty acid having 8 to 28 carbon atoms is preferred, one having 12 to 22 carbon atoms is more preferred, and one having 16 to 18 carbon atoms is particularly preferred. Furthermore, for the branched structure of the branched saturated fatty acid, both a methyl-branched type and a multi-branched type can be used. When the number of carbon atoms of the branched saturated fatty acid is within the range described above, the gelation ability for the cyclic silicone or volatile dimethylpolysiloxane and the oil agent is favorable. Also, the sense of touch is favorable when used in cosmetic preparations.

Specific examples of the branched saturated fatty acid include isooctylic acid, isopalmitic acid, isostearic acid, isoeicosanoic acid, and the like. In particular, isostearic acid of methyl-branched type is preferred in terms of the sense of touch when used in cosmetic preparations.

(Hydroxyl Value)

The hydroxyl value of the esterification reaction product is 30 or less, preferably 20 or less, and particularly preferably 10 or less. When the hydroxyl value of the esterification reaction product is within the range described above, the gelation ability of the cyclic silicone or volatile dimethylpolysiloxane and the oil agent is favorable. Additionally, the hydroxyl value is a value obtainable by the hydroxyl value measurement method among the General Test Methods described in the Japanese Standards of Cosmetic Ingredients, Newly Revised Edition (JSCI).

[Method for producing Esterification Reaction Product According to Embodiments of Present Invention]

The esterification reaction product according to an embodiment of the present invention is obtainable by subjecting the polyhydric alcohol or a condensate thereof of component A, the saturated dibasic acid of component B, the linear saturated fatty acid of component C, and the branched saturated fatty acid of component D, to esterification reaction, and for example, can be produced by the following method.

The polyhydric alcohol or a condensate thereof of component A, the saturated dibasic acid of component B, the linear saturated fatty acid of component C, and the branched saturated fatty acid of component D are introduced into a reaction vessel, and an esterification reaction is carried out at 160 to 240° C. under an inert gas stream for about 5 to 30 hours, while removing the water generated from the reaction. After completion of the esterification reaction, purification treatments such as decoloration and deodorization are carried out by conventional methods, and thereby, an esterification reaction product may be obtained.

During the esterification reaction, an acid catalyst, a metal catalyst, and a reflux solvent can be used according to necessity.

The completion point of reaction of the esterification reaction can be easily monitored from the feed ratios of the raw materials that are the polyhydric alcohol or a condensate thereof of component A, the saturated dibasic acid of component B, the linear saturated fatty acid of component C and the branched saturated fatty acid of component D, and the acid value during the esterification reaction. Furthermore, the resulting esterification reaction product is a product having fewer odors and less coloration.

In the esterification reaction, particularly the blending ratio of the polyhydric alcohol or a condensate thereof of component A and the saturated dibasic acid of component B is important, and the blending ratio of the polyhydric alcohol or a condensate thereof of component A and the saturated dibasic acid of component B is preferably such that, relative 1.0 mole of component A, the component B is used in an amount of 0.10 to 0.20 moles, more preferably 0.12 to 0.18 moles, and particularly preferably 0.15 to 0.17 moles. When the blending ratio of the component A and the component B is within the range described above, the gelation ability for the cyclic silicone or volatile dimethylpolysiloxane and the oil agent, and the gelation ability for the oil agent are favorable.

In the esterification reaction, the blending ratio of the polyhydric alcohol or a condensate thereof of component A and the linear saturated fatty acid of component C is preferably such that, relative to 1.0 mole of the component A, the component C is used in an amount of 1.0 to 7.5 moles, more preferably 1.3 to 3.0 moles, and particularly preferably 1.5 to 2.5 moles. When the blending ratio of the component A and the component C is within the range described above, the gelation ability for the cyclic silicone or volatile dimethylpolysiloxane and the oil agent, and the gelation ability for the oil agent are favorable.

In the esterification reaction, the blending ratio of the polyhydric alcohol or a condensate thereof of component A and the branched saturated fatty acid of component D is preferably such that, relative to 1.0 mole of the component A, the component D is used in an amount of 0.2 to 2.3 moles, more preferably 0.3 to 1.5 moles, and particularly preferably 0.5 to 1.0 mole. When the blending ratio of the component A and the component D is within the range described above, the gelation ability for the cyclic silicone or volatile dimethylpolysiloxane and the oil agent, and the gelation ability for the oil agent are favorable. Furthermore, the sense of touch is favorable when used in cosmetic preparations.

[Properties, Applications and Form of Use of Esterification Reaction Product According to Embodiments of Present Invention]

The esterification reaction product according to the present embodiment has good solubility under heating in a cyclic silicone or a volatile dimethylpolysiloxane.

Here, according to the present embodiment, the phrase "has good solubility under heating" implies that if the total mass of the cyclic silicone or volatile dimethylpolysiloxane at 70° C. is considered as 1, the esterification reaction product according to the present embodiment is dissolved under heating at least until the mass ratio reaches 1.

Furthermore, the esterification reaction product according to the present embodiment described above is able to gelate both a cyclic silicone or volatile dimethylpolysiloxane and an oil agent, and thus can be used as a gelling agent for these. Therefore, the reaction product can be used in formulas which require gelation of both a cyclic silicone or a volatile dimethylpolysiloxane and an oil agent.

The esterification reaction product according to the present embodiment can also gelate certain polyether-modified silicones (for example, KF-6017 and KF-6015 manufactured by Shin-Etsu Chemical Co., Ltd.; and SILSOFT 305 manufactured by GE Toshiba Silicones Co., Ltd.), or methylphenylpolysiloxanes (for example, KF-56 manufactured by Shin-Etsu Chemical Co., Ltd.) used for the use in cosmetic preparations which can also be gelated by conventional gelling agents.

Here, according to the present embodiment, gelation means that a cyclic silicone, a volatile dimethylpolysiloxane, an oil agent or the like can be gelated or solidified. The cyclic silicone means a silicone having a cyclic molecular structure. The volatile dimethylpolysiloxane means that a dimethylpolysiloxane which is volatile at normal temperature (dimethylpolysiloxane may also be referred to as methylpolysiloxane). Furthermore, the oil agent means an ester oil agent, a hydrocarbon, fat, wax, or the like.

In regard to the esterification reaction product according to the present embodiment, the esterification product not only can be used alone as a gelling agent, but also can be used as a gel-like composition which is in combination with other components. This gel-like composition can be obtained by combining the esterification reaction product according to the present embodiment with other components. As the other components, oil agents and the like may be mentioned, and specific examples thereof include ester oil agents such as glyceryl tri-2-ethylhexanoate (common name: trioctanoin), octyl palmitate, cetyl octanoate, isononyl isononanoate, isotridecyl isononanoate, neopentyl glycol didecanoate, and polyglyceryl-2 triisostearate; and hydrocarbons such as liquid paraffin, light liquid isoparaffin, and heavy liquid isoparaffin. This gel-like composition can be obtained by mixing under heating the esterification reaction product according to the present embodiment in some other substance in advance, and dispersing and dissolving the reaction product therein. Since this gel-like composition has the esterification reaction product according to the present embodiment dispersed and dissolved in an oil agent in advance, the composition has improved handlability.

The esterification reaction product according to the present embodiment alone has poor solubility under heating in a non-volatile dimethylpolysiloxane, but when the esterification reaction product according to the present embodiment is used in combination with an oil agent, the solubility under heating in the non-volatile dimethylpolysiloxane becomes good. Furthermore, when the reaction product is used in combination with an oil agent, the combination is capable of gelating both the non-volatile dimethylpolysiloxane and the oil agent, and the combination can be used as a gelling agent for those. The non-volatile dimethylpolysiloxane means a dimethylpolysiloxane which is non-volatile at normal temperature (the dimethylpolysiloxane may also be referred to as methylpolysiloxane).

Among specific examples of the oil agent which can be used in order to dissolve the esterification reaction product according to the present embodiment in a non-volatile dimethylpolysiloxane under heating, or to gelate a non-volatile dimethylpolysiloxane, preferred ones include isononyl isononanoate, isotridecyl isononanoate, glyceryl tri-2-ethylhexanoate, neopentyl glycol didecanoate, neopentyl glycol 2-ethylhexanoate, pentaerythrityl tetraoctanoate, erythrityl triethylhexanoate, liquid paraffin, and the like.

The esterification reaction product according to the present embodiment imparts thixotropic properties to a formula containing an oil agent such as liquid paraffin, glyceryl tri-2-ethylhexanoate, octyl palmitate, cetyl octanoate or dicaprylyl carbonate, and therefore, the reaction product can be used as a thixotropy imparting agent. Thixotropy is an isothermal reversible sol (liquid)-gel (solid) change, and implies that a solid substance is converted to liquid by an external force. That is, a substance having thixotropic properties is usually solid, but when force is applied, the substance becomes liquid. Therefore, when a substance having thixotropic properties is filled in a plastic container or the like, the substance does not usually spill over from the container or the like, but can be extruded only when necessary. Furthermore, a substance having thixotropic properties can be freely applied and spread out at the time of use. Specific examples of those substances having thixotropic properties include ketchup, creams, perfumes in the field of toiletries, paint, and the like.

Furthermore, since the esterification reaction product according to the present embodiment has an effect of enhancing the emulsion stability of water-in-oil type (W/O type) emulsions, the reaction product can be used as an emulsion stabilizer. When the esterification reaction product according to the present embodiment is incorporated, a water-in-oil type emulsion having excellent stability over time and good feeling of use can be obtained. In this case, the content of the esterification reaction product is preferably 0.01 to 40% by mass, more preferably 0.05 to 30% by mass, and particularly preferably 0.1 to 15% by mass, when the total amount of the emulsion is taken as 100% by mass.

[Gelling Agent According to Embodiments of Present Invention]

The gelling agent according to an embodiment of the present invention is characterized by containing the esterification reaction product according to the present embodiment. The gelling agent may also contain the above-described gel-like composition combined with an oil agent and the like.

In regard to the gelling agent according to an embodiment of the present invention, usually the esterification reaction product according to the present embodiment is directly used as a gelling agent (the gelling agent comprises the esterification reaction product only, so that the content of the esterification reaction product in the gelling agent is 100%), but tocopherol, BHT (dibutylhydroxytoluene) or the like may also be contained as an antioxidant in an amount of about 0.01% by mass to 0.1% by mass.

Specific examples of the cyclic silicone that can be gelated by the gelling agent according to the present embodiment, include octamethylcyclotetrasiloxane, decamethylcyclopentasiloxane, dodecamethylcyclohexasiloxane and the like, and in particular, decamethylcyclopentasiloxane can be suitably gelated. Specific examples which are capable of dissolution under heating are also similar.

Specific examples of the volatile dimethylpolysiloxane which can be gelated by the gelling agent according to the present embodiment, include dimethylpolysiloxane 2 cs, dimethylpolysiloxane 1 cs, and the like, and in particular, dimethylpolysiloxane 2 cs can be suitably gelated (cs represents the viscosity, and 1 cs=1 mm$^2$/s. Hereinafter, the same.) Specific examples which are capable of dissolution under heating are also similar.

Specific examples of the oil agent which can be gelated by the gelling agent according to the present embodiment, include ester oil agents such as diisostearyl malate, glyceryl tri-2-ethylhexanoate, polyglyceryl monoisostearate, polyglyceryl diisostearate, polyglyceryl triisostearate, polyglyceryl tetraisostearate, ethylhexyl palmitate, cetyl octanoate, isononyl isononanoate, isotridecyl isononanoate, isostearyl myristate, neopentyl glycol diethylhexanoate, neopentyl glycol didecanoate, glyceryl tri(octanoate/decanoate), tri isostearin, trimethylolpropane triisostearate, pentaerythrityl tetraoctanoate, pentaerythrityl tetraisostearate, octyl dodecyl lactate, (isostearic acid/sebacic acid) ditrimethylolpropane oligoester, ditrimethylolpropane triethylhexanoate, and erythrityl triethylhexanoate; hydrocarbon oil agents such as hydrogenated polyisobutene, isoparaffin, polybutene, liquid paraffin, squalane, and olefin oligomers; and the like. In particular, isostearyl malate, glyceryl tri-2-ethylhexanoate, polyglyceryl triisostearate, ethylhexyl palmitate, neopentyl glycol didecanoate, liquid paraffin, and isododecane can be suitably gelated.

Specific examples of the non-volatile dimethylpolysiloxane which can be gelated by combining the gelling agent according to the present embodiment and an oil agent, include dimethylpolysiloxane 5 cs, dimethylpolysiloxane 10 cs, and dimethylpolysiloxane 100 cs. Specific examples which are capable of dissolution under heating are also similar.

If the total mass of the cyclic silicone or volatile dimethylpolysiloxane is considered as 1, the gelling agent according to the present embodiment is dissolved under heating at least until the mass ratio reaches 1.

The amount of the gelling agent required to gelate the cyclic silicone or volatile dimethylpolysiloxane and the oil agent, depends on the total amount of the cyclic silicone or volatile dimethylpolysiloxane and the oil agent. The blending ratio (mass ratio) of the gelling agent with respect to the total mass of the cyclic silicone or volatile dimethylpolysiloxane and the oil agent, is preferably 0.01 to 0.40, more preferably 0.015 to 0.25, and particularly preferably 0.02 to 0.15, if the total mass of the cyclic silicone or volatile dimethylpolysiloxane and the oil agent is considered as 1.

The gelling agent according to the present embodiment is not limited to the combined formula of the cyclic silicone or volatile dimethylpolysiloxane and the oil agent, but can also be used as a gelling agent for an individual formula of a cyclic silicone or volatile dimethylpolysiloxane alone or of an oil agent alone.

Furthermore, the amount of the oil agent required for favorably dissolving the gelling agent under heating in the non-volatile dimethylpolysiloxane, depends on the amount of the non-volatile dimethylpolysiloxane. The blending ratio (mass ratio) of the oil agent with respect to the non-volatile dimethylpolysiloxane is preferably 0.4 to 10.0, more preferably 0.5 to 10.0, and particularly preferably 0.6 to 10.0, if the mass of the non-volatile dimethylpolysiloxane is considered as 1. When the blending ratio of the oil agent to the mass of the non-volatile dimethylpolysiloxane is within this range, if the total mass of the non-volatile dimethylpolysiloxane and the oil agent is considered as 1, the gelling agent according to the present embodiment is dissolved under heating at least until the mass ratio reaches 1.

Furthermore, the amount of the gelling agent according to the present embodiment required to gelate the non-volatile dimethylpolysiloxane and the oil agent, depends on the total amount of the non-volatile dimethylpolysiloxane and the oil agent. The blending ratio (mass ratio) of the gelling agent according to the present embodiment with respect to the total mass of the non-volatile dimethylpolysiloxane and the oil agent is preferably 0.03 to 0.40, more preferably 0.05 to 0.30, and particularly preferably 0.10 to 0.20, if the total mass of the non-volatile dimethylpolysiloxane and the oil agent is considered as 1.

The gelling agent according to the present embodiment can be used for cosmetic preparations, treatment agents for oil agents, treatment agents for pigments, treatment agents for dyes, emulsion stabilizers, thixotropy imparting agent, friction improving agents for silicone, and the like. In particular, the gelling agent can be suitably used in cosmetic preparations.

[Thixotropy Imparting Agent According to Embodiment of Present Invention]

In regard to the thixotropy imparting agent according to the present embodiment, usually, the esterification reaction product or the gelling agent according to the present embodiment is used directly as the thixotropy imparting agent (the thixotropy imparting agent comprising only the esterification reaction product or the gelling agent, and thus the content of the esterification reaction product or the gelling agent in the thixotropy imparting agent is 100%), but tocopherol, BHT (dibutylhydroxytoluene) and the like may also be contained as antioxidants in an amount of 0.01% by mass to 0.1% by mass (hereinafter, the case where a gelling agent having a content of the esterification reaction product of 100% is used directly as the thixotropy imparting agent, will be described). The blending ratio of the gelling agent required to impart thixotropic properties, depends on the total amount of the oil agent. The blending ratio (mass ratio) of the gelling agent with respect to the total mass of the oil agent is preferably 0.04 to 0.25, more preferably 0.045 to 0.20, and particularly preferably 0.05 to 0.15, if the total mass of the oil agent is considered as 1.

[Cosmetic Preparation According to Embodiment of Present Invention]

The cosmetic preparation according to an embodiment of the present invention contains the gelling agent according to the present embodiment (in the following description on the blending amount of the gelling agent, the case of using the esterification reaction product directly as the gelling agent will be described. In the case where the gelling agent contains substances other than the esterification reaction product, the blending amount may vary depending on the type of the containing substances other than the esterification reaction product, or the like, but in general, a preferred blending amount can be calculated from the following blending amount, based on the rule-of-three sum). The blending amount of the gelling agent in a cosmetic preparation is preferably 0.01 to 40% by mass, more preferably 0.05 to 30% by mass, and particularly preferably 0.1 to 15% by mass, based on the total amount of the cosmetic preparation. When the blending amount of the gelling agent in a cosmetic preparation is within this range, the feeling of use of the cosmetic preparation is good, and the cosmetic preparation does not have the frictional feeling of silicone.

The cosmetic preparation according to the present embodiment contains a cyclic silicone or a volatile dimethylpolysiloxane, and/or an oil agent. The cyclic silicone, volatile dimethylpolysiloxane and the oil agent used in the cosmetic preparation according to the present embodiment are similar to the cyclic silicone, volatile dimethylpolysiloxane and the oil agent which can be gelated by the above-described gelling agent according to the present embodiment.

Furthermore, the cosmetic preparation according to the present embodiment contains a non-volatile dimethylpolysiloxane and an oil agent. The non-volatile dimethylpolysiloxane can be gelated by the gelling agent according to the present embodiment when combined with an oil agent. The non-volatile dimethylpolysiloxane used in the cosmetic preparation according to the present embodiment, and the oil agent which can be used for gelating the non-volatile dimethylpolysiloxane, are similar to the above-described non-volatile dimethylpolysiloxane which can be gelated by the gelling agent according to the present embodiment and the above-described oil agent capable of gelating the non-volatile dimethylpolysiloxane.

The contents of the cyclic silicone and volatile dimethylpolysiloxane in the cosmetic preparation according to the present embodiment are, in total, preferably 0.1 to 95% by mass, more preferably 0.5 to 60% by mass, particularly preferably 1 to 30% by mass, and most preferably 1 to 10% by mass. When the contents of the cyclic silicone and volatile dimethylpolysiloxane in the cosmetic preparation are within this range, a cosmetic preparation which is excellent in smoothness, sense of touch and beauty aspects such as gloss, is obtained.

The content of the non-volatile dimethylpolysiloxane in the cosmetic preparation according to the present embodiment is, in total, preferably 0.1 to 80% by mass, more preferably 0.5 to 60% by mass, particularly preferably 1 to 30% by mass, and most preferably 1 to 10% by mass. When the content of the non-volatile dimethylpolysiloxane in the cosmetic preparation is within this range, a cosmetic preparation is obtained, which does not give the frictional feeling of silicone and is excellent in smoothness, sense of touch and beauty aspects such as gloss.

The content of the oil agent in the cosmetic preparation according to the present embodiment is preferably 0.1 to 99% by mass, more preferably 0.5 to 95% by mass, and particularly preferably 1 to 90% by mass. When the content of the oil agent in the cosmetic preparation is within this range, a cosmetic preparation which is excellent in smoothness, sense of touch and beauty aspects such as gloss, is obtained.

The gelling agent according to the present embodiment can be suitably used in cosmetic preparations having a formula in which a cyclic silicone or volatile dimethylpolysiloxane, and/or an oil agent is blended, specifically for formulation forms which require gelation or solidification.

Furthermore, the gelling agent according to the present embodiment can be suitably used in cosmetic preparations having a formula in which a non-volatile dimethylpolysiloxane is blended, specifically for formulation forms which require gelation or solidification, by being combined with an oil agent. In particular, the gelling agent can be suitably used in oily cosmetic preparations.

Furthermore, since the gelling agent according to the present embodiment has an effect of enhancing the emulsion stability of water-in-oil type emulsions, the gelling agent can be suitably used as an emulsion stabilizer in water-in-oil type emulsified cosmetic preparations.

Moreover, since the gelling agent according to the present embodiment can impart thixotropic properties, the gelling agent can be suitably used as a thixotropy imparting agent in cosmetic preparations requiring thixotropic properties, for example, in creams, and the like.

Specifically, lipsticks, lip glosses; creams such as lip creams, hand creams, cosmetic creams, and hair creams; cosmetic solutions, emulsions, lotions, foundations, controls, sunscreens (sunburn preventive cosmetic preparations), blushers, base cosmetic preparations, eye shadows, eyebrows, mascaras, shampoos, rinses such as hair rinses, conditioners, cleansing products, hair dressing products such as hair waxes, manicure preparations, cosmetic preparations having anti-wrinkle effects, and aerosols may be mentioned, and particularly, the gelling agent may be suitably incorporated into lipsticks, creams, emulsions, foundations and sunscreens.

The cosmetic preparation according to the present embodiment can be produced by the known standard methods for the respective formulation forms.

In the cosmetic preparation according to the present embodiment, components that are conventionally used in cosmetic preparations, including silicone compounds such as polyether-modified silicones, alkyl-modified silicones, and methylphenyl polysiloxanes; alcohols such as cetanol and oleyl alcohol; higher fatty acids; esters such as fatty acid soaps, sterol esters, sucrose esters; resins; amino acid-based oil agents, fluorine-based oil agents, pigments, dyes, colors, coloring agents, powders, clay minerals, inorganic components, activating agents, ultraviolet absorbents, moisturizing agents, fragrances, cosmetic components, medicinal components, antioxidants, antiseptics, water, and water-soluble polymers, can be incorporated, in addition to the gelling agent according to the present embodiment, cyclic silicone, volatile dimethylpolysiloxane, non-volatile dimethylpolysiloxane and oil agent.

A cosmetic preparation containing the gelling agent according to the present embodiment results in a preparation which is excellent in the feeling of use such as the sense of touch, spreading, feeling of stickiness, smoothness and fresh sensation, colorability, gloss, and maintenance of make-up, and has no frictional feeling of silicone.

EXAMPLES

Example 1

In a four-necked flask having a volume of 2 liters, 92 g (1.0 mole) of glycerin, 55 g (0.16 moles) of eicosanedioic acid, 680 g (2.0 moles) of behenic acid, and 173 g (0.6 moles) of methyl-branched type isostearic acid were introduced, and 0.01% (0.1 g) of p-toluenesulfonic acid was introduced as a catalyst. Under a nitrogen stream as an inert gas, the temperature was maintained at 180 to 210° C., and an esterification reaction was carried out for 16 hours while stirring, until the acid value of the reactant did not decrease any more. Subsequently, a deodorization treatment was carried out by blowing in steam for 1 hour, to thus obtain 753 g of an esterification reaction product. This esterification reaction product had an acid value of 2.2, a saponification value of 169, and a hydroxyl value of 3.0. The obtained esterification reaction product was designated as the gelling agent of Example 1.

Examples 2 to 16 and Comparative Examples 1 to 10

Esterification reaction products were also obtained in Examples 2 to 16 and Comparative Examples 1 to 10, where the blending raw materials and the blending ratios were changed, by the same production method as in Example 1. The obtained esterification reaction products were designated as the gelling agents of Examples 2 to 16 and Comparative Examples 1 to 10. Additionally, an esterification reaction product could not be obtained in Comparative Example 6 because the raw material isohexanoic acid boiled during the reaction.

The blending raw materials, feed amounts and blending ratios of Examples 1 to 16 and Comparative Examples 1 to 10 are presented in Table 1.

Additionally, in regard to the raw materials used, glycerin: concentrated glycerin for cosmetic products, manufactured by Sakamoto Yakuhin Kogyo Co., Ltd.; eicosanedioic acid: SL-20 manufactured by Okamura Oil Mill, Ltd.; behenic acid: PRIFRAC 2989 manufactured by Unichema Corporation; methyl-branched type isostearic acid: Emersol 874 manufactured by Cognis Corporation; multi-branched type isostearic acid: isostearic acid manufactured by Nissan Chemical Industries, Ltd.; octadecanedioic acid: Emerox 118 manufactured by Cognis Corporation; isooctanoic acid: octanoic acid manufactured by Chisso Corporation; trimethylolpropane: trimethylolpropane manufactured by Koei Chemical Co., Ltd.; stearic acid: PALMAC 98-18 manufactured by Acidchem International Snd. Bhd.; montanoic acid: Hoechest WAX S manufactured by Clariant (Japan) K.K.; sebacic acid: sebacic acid manufactured by Kokura Synthetic Industries, Ltd.; diglycerin: DIGLYCERIN S manufactured by Sakamoto Yakuhin Kogyo Co., Ltd.; decaglycerin: POLYGLYCERIN #750 manufactured by Sakamoto Yakuhin Kogyo Co., Ltd.; succinic anhydride: RIKACID SA manufactured by New Japan Chemical Co., Ltd.; lauric acid: PALMAC 98-12 manufactured by Acidchem International Snd. Bhd.; palmitic acid: PALMAC 98-16 manufactured by Acidchem International Snd. Bhd.; and isohexanoic acid: 2-ethylbutyric acid manufactured by Chisso Corporation were used.

(Evaluation of Gelation Ability 1)

In order to evaluate the gelation ability of the gelling agents of Examples 1 to 16 and Comparative Examples 1 to 5 and 7 to 10 on a cyclic silicone, the state of gelation products obtained by adding 1 g each of the gelling agents of Examples 1 to 16 and Comparative Examples 1 to 5 and 7 to 10 to 10 g of decamethylcyclopentasiloxane (KF-995 manufactured by Shin-Etsu Chemical Co., Ltd.), dissolving the mixtures under heating at 80° C., and then leaving the mixtures to cool at room temperature, was evaluated. The results are presented in Table 1.

The evaluation criteria for the state of the gelation products were as follows.

⊚: complete solidification, ○: gelation, Δ: dispersed liquid, x: complete separation

TABLE 1

| | | Number of grams of raw materials used for esterification reaction product (blending ratio (moles)) | | | | | |
|---|---|---|---|---|---|---|---|
| | | Component A Polyhydric alcohol or condensate thereof | Component B Saturated dibasic acid | Component C Linear saturated fatty acid | Component D Branched saturated fatty acid | State of gelation product | Hydroxyl value of esterification reaction product |
| Example | 1 | Glycerin 92 g (1.0) | Eicosanedioic acid 55 g (0.16) | Behenic acid 680 g (2.0) | Methyl-branched isostearic acid 173 g (0.6) | ⊚ | 3.0 |
| | 2 | Glycerin 92 g (1.0) | Eicosanedioic acid 55 g (0.16) | Behenic acid 680 g (2.0) | Multi-branched isostearic acid 173 g (0.6) | ⊚ | 4.8 |
| | 3 | Glycerin 92 g (1.0) | Eicosanedioic acid 55 g (0.16) | Behenic acid 510 g (1.5) | Methyl-branched isostearic acid 317 g (1.1) | ⊚ | 4.8 |
| | 4 | Glycerin 92 g (1.0) | Octadecanedioic acid 50 g (0.16) | Behenic acid 680 g (2.0) | Methyl-branched isostearic acid 173 g (0.6) | ⊚ | 9.4 |
| | 5 | Glycerin 92 g (1.0) | Eicosanedioic acid 68 g (0.2) | Behenic acid 680 g (2.0) | Methyl-branched isostearic acid 144 g (0.5) | ⊚ | 7.1 |
| | 6 | Glycerin 92 g (1.0) | Eicosanedioic acid 55 g (0.16) | Palmitic acid 513 g (2.0) | Methyl-branched isostearic acid 173 g (0.6) | ⊚ | 5.6 |
| | 7 | Glycerin 92 g (1.0) | Eicosanedioic acid 55 g (0.16) | Behenic acid 680 g (2.0) | Isooctylic acid 86.4 g (0.6) | ⊚ | 6.3 |
| | 8 | Trimethylolpropane 134 g (1.0) | Eicosanedioic acid 68 g (0.2) | Behenic acid 782 g (2.3) | Methyl-branched isostearic acid 58 g (0.2) | ⊚ | 9.1 |

TABLE 1-continued

Number of grams of raw materials used for esterification reaction product (blending ratio (moles))

| | | Component A Polyhydric alcohol or condensate thereof | Component B Saturated dibasic acid | Component C Linear saturated fatty acid | Component D Branched saturated fatty acid | State of gelation product | Hydroxyl value of esterification reaction product |
|---|---|---|---|---|---|---|---|
| | 9 | Glycerin 92 g (1.0) | Eicosanedioic acid 55 g (0.16) | Behenic acid 340 g (1.0) Stearic acid 284 g (1.0) | Methyl-branched isostearic acid 173 g (0.6) | ○ | 9.6 |
| | 10 | Glycerin 92 g (1.0) | Eicosanedioic acid 34 g (0.1) | Behenic acid 850 g (2.5) | Methyl-branched isostearic acid 58 g (0.2) | ⊚ | 5.3 |
| | 11 | Trimethylolpropane 134 g (1.0) | Eicosanedioic acid 34 g (0.1) | Behenic acid 850 g (2.5) | Methyl-branched isostearic acid 58 g (0.2) | ○ | 7.8 |
| | 12 | Glycerin 92 g (1.0) | Eicosanedioic acid 55 g (0.16) | Montanic acid 424 g (2.0) | Methyl-branched isostearic acid 173 g (0.6) | ⊚ | 8.9 |
| | 13 | Glycerin 92 g (1.0) | Sebacic acid 32 g (0.16) | Behenic acid 680 g (2.0) | Methyl-branched isostearic acid 173 g (0.6) | ⊚ | 7.9 |
| | 14 | Diglycerin 166 g (1.0) | Eicosanedioic acid 55 g (0.16) | Behenic acid 901 g (2.65) | Methyl-branched isostearic acid 144 g (1.0) | ⊚ | 13.5 |
| | 15 | Decaglycerin 940 g (1.0) | Eicosanedioic acid 55 g (0.16) | Behenic acid 2550 g (7.5) | Methyl-branched isostearic acid 662 g (2.3) | ⊚ | 19.2 |
| | 16 | Glycerin 92 g (1.0) | Eicosanedioic acid 55 g (0.16) | Behenic acid 884 g (2.6) | — | ⊚ | 6.4 |
| Comparative Example | 1 | Glycerin 92 g (1.0) | Eicosanedioic acid 103 g (0.3) | Behenic acid 408 g (1.2) | Methyl-branched isostearic acid 331 g (1.15) | Δ | 5.3 |
| | 2 | Decaglycerin 940 g (1.0) | Eicosanedioic acid 86 g (0.25) | Behenic acid 3060 g (9.0) | Methyl-branched isostearic acid 331 g (1.15) | x | 23.6 |
| | 3 | Trimethylolpropane 134 g (1.0) | Eicosanedioic acid 103 g (0.3) | Behenic acid 408 g (1.2) | Methyl-branched isostearic acid 331 g (1.15) | Δ | 6.9 |
| | 4 | Glycerin 92 g (1.0) | Eicosanedioic acid 17 g (0.05) | Behenic acid 714 g (2.1) | Methyl-branched isostearic acid 216 g (0.75) | Δ | 4.9 |
| | 5 | Glycerin 92 g (1.0) | Eicosanedioic acid 55 g (0.16) | Lauric acid 400 g (2.0) | Methyl-branched isostearic acid 173 g (0.6) | Δ | 8.3 |
| | 6 | Glycerin 92 g (1.0) | Eicosanedioic acid 55 g (0.16) | Behenic acid 680 g (2.0) | Isohexanoic acid 70 g (0.6) | — | — |
| | 7 | Glycerin 92 g (1.0) | Succinic anhydride 16 g (0.16) | Behenic acid 680 g (2.0) | Methyl-branched isostearic acid 173 g (0.6) | Δ | 9.1 |
| | 8 | Glycerin 92 g (1.0) | Eicosanedioic acid 55 g (0.16) | Behenic acid 480 g (1.2) | Methyl-branched isostearic acid 259 g (0.9) | Δ | 37.7 |
| | 9 | Glycerin 92 g (1.0) | Eicosanedioic acid 171 g (0.5) | Behenic acid 680 g (2.0) | — | x | 7.1 |
| | 10 | Glycerin 92 g (1.0) | Eicosanedioic acid 239 g (0.7) | Behenic acid 510 g (1.5) | — | x | 8.8 |

As can be seen from Table 1, the gelling agents of Examples 1 to 16, which are esterification reaction products obtainable by subjecting the component A to the component D in the amounts within the prescribed ranges, to an esterification reaction at a blending ratio in the prescribed range, could gelate the cyclic silicone, and yielded satisfactory results. From Example 16, it was understood that if the components A to the component C were blended at a blending ratio in the prescribed range, even though the component D was not used, gelation was achieved favorably.

On the other hand, the gelling agents of Comparative Examples 1 to 4, 9 and 10, in which the blending ratio of the component A and the component B at the time of the esterification reaction was out of the prescribed range; the gelling agents of Comparative Examples 5 and 7, in which a component B and a component C having fewer carbon numbers than the prescribed ranges were used; and the gelling agent of Comparative Example 8, in which the hydroxyl value was out of the prescribed range, could not gelate the cyclic silicone, and did not yield satisfactory results.

(Evaluation of Gelation Ability 2)

1 g each of the gelling agents of Examples 1 to 9, Comparative Examples 1 to 5, and Comparative Examples 8 and 9 was added to 9 g each of various silicones and oil agents, and these samples were used as evaluation samples.

The evaluation samples were heated for 1 hour in a constant temperature bath at 80° C., and then these samples were mixed to uniformly dissolve the gelling agents in the oil agents. The uniformly dissolved evaluation samples were stored at 25° C. for 24 hours, and then the state of gelation products was evaluated. The results are presented in Table 2.

The evaluation criteria of the state of the gelation products were as follows.

⊚: complete solidification, ○: gelation, Δ: dispersed liquid, x: complete separation

TABLE 2

| | State of gelation product | | | | | | | | | | | | | | | |
|---|---|---|---|---|---|---|---|---|---|---|---|---|---|---|---|---|
| Names of various silicones and oil | Example | | | | | | | | | Comparative Example | | | | | | |
| agents used | 1 | 2 | 3 | 4 | 5 | 6 | 7 | 8 | 9 | 1 | 2 | 3 | 4 | 5 | 8 | 9 |
| Dimethylpolysiloxane 2 cs (volatile dimethylpolysiloxane) *1 | ⊚ | ⊚ | ⊚ | ⊚ | ⊚ | ⊚ | ⊚ | ⊚ | ⊚ | Δ | x | Δ | x | x | Δ | x |

TABLE 2-continued

| Names of various silicones and oil agents used | State of gelation product | | | | | | | | | | | | | | | |
|---|---|---|---|---|---|---|---|---|---|---|---|---|---|---|---|---|
| | Example | | | | | | | | | Comparative Example | | | | | | |
| | 1 | 2 | 3 | 4 | 5 | 6 | 7 | 8 | 9 | 1 | 2 | 3 | 4 | 5 | 8 | 9 |
| Methylphenyl polysiloxane (other silicone) *2 | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ |
| Polyether-modified silicone (other silicone) *3 | ⊚ | ⊚ | ○ | ○ | ⊚ | ○ | ○ | ⊚ | ○ | ○ | ○ | ○ | ○ | △ | △ | x |
| Glyceryl tri-2-ethylhexanoate (oil agent) *4 | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ |
| Diisostearyl malate (oil agent) *5 | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ |
| Diglyceryl triisostearate (oil agent) *6 | ⊚ | ⊚ | ⊚ | ⊚ | ⊚ | ⊚ | ○ | ⊚ | ⊚ | ⊚ | ⊚ | ⊚ | ⊚ | ⊚ | ⊚ | ⊚ |
| Diglyceryl diisostearate (oil agent) *7 | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ |
| Ethylhexyl palmitate (oil agent) *8 | ⊚ | ⊚ | ○ | ○ | ⊚ | ○ | ⊚ | ⊚ | ⊚ | ⊚ | ⊚ | ⊚ | ⊚ | ⊚ | ○ | ⊚ |
| Cetyl octanoate (oil agent) *9 | ⊚ | ⊚ | ○ | ○ | ⊚ | ○ | ⊚ | ⊚ | ⊚ | ⊚ | ⊚ | ⊚ | ⊚ | ⊚ | ○ | ⊚ |
| Neopentyl glycol diethylhexanoate (oil agent) *10 | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ |
| Neopentyl glycol dicaprate (oil agent) *11 | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ |
| Pentaerythrityl tetraoctanoate (oil agent) *12 | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ |
| Isoparaffin (oil agent) *13 | ○ | ○ | ○ | ○ | ○ | ○ | ○ | ○ | ○ | ○ | ○ | ○ | ○ | ○ | ○ | ⊚ |
| Liquid paraffin (oil agent) *14 | ○ | ○ | ○ | ○ | ⊚ | ○ | ○ | ○ | ○ | ○ | ○ | ○ | ○ | ○ | ○ | ⊚ |
| Polybutene (oil agent) *15 | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ | ⊚ |

For the reference numerals *1 to *15 in Table 2, the following products were used.
*1: KF-96 2cs manufactured by Shin-Etsu Chemical Co., Ltd.
*2: KF-56 manufactured by Shin-Etsu Chemical Co., Ltd.
*3: KF-6017 and KF-6015 manufactured by Shin-Etsu Chemical Co., Ltd., SILSOFT 305 manufactured by GE Toshiba Silicones Co., Ltd., the three species all gave the same results.
*4: T.I.O. manufactured by Nisshin OilliO Group, Ltd.
*5: COSMOL 222 manufactured by Nisshin OilliO Group, Ltd.
*6: COSMOL 43V manufactured by Nisshin OilliO Group, Ltd.
*7: COSMOL 42V manufactured by Nisshin OilliO Group, Ltd.
*8: SALACOS P-8 manufactured by Nisshin OilliO Group, Ltd.
*9: SALACOS 816T manufactured by Nisshin OilliO Group, Ltd.
*10: COSMOL 525 manufactured by Nisshin OilliO Group, Ltd.
*11: ESTEMOL N-01 manufactured by Nisshin OilliO Group, Ltd.
*12: SALACOS 5408 manufactured by Nisshin OilliO Group, Ltd.
*13: IP SOLVENT-1620 manufactured by Idemitsu Petrochemical Co., Ltd.
*14: CARNATION manufactured by Shima Trading Co., Ltd.
*15: PARLEAM 18 manufactured by Nippon Oil and Fat Co., Ltd.

As can be seen from Table 2, the gelling agents of Examples 1 to 9, which are esterification reaction products obtainable by subjecting the component A through the component D in the amounts within the prescribed ranges, to an esterification reaction at a blending ratio in the prescribed range, could gelate the volatile dimethylpolysiloxanes and the oil agents, and yielded satisfactory results.

On the other hand, the gelling agents of Comparative Examples 1 to 4 and 9, in which the blending ratio of the component A and the component B at the time of the esterification reaction was out of the prescribed range, and the gelling agent of Comparative Example 5, in which a component C having fewer carbon atoms than the prescribed range was used, could not gelate the volatile dimethylpolysiloxanes, and did not yield satisfactory results. Furthermore, the gelling agent of Comparative Example 8, in which the hydroxyl value was out of the prescribed range, could gelate the oil agents but could not gelate the volatile dimethylpolysiloxanes, and did not yield satisfactory results.

(Evaluation of Cosmetic Preparation 1)

Example 1 and Comparative Example 9 were used to produce foundations of Example 17 and Comparative Example 11 by the following method, and an evaluation thereof was performed.

While sufficiently stirring the oily components A indicated in Table 3, the pigment base B indicated in the same Table 3 was added to prepare an oil phase, and then the aqueous components C indicated in the same Table 3 were slowly added to the prepared oil phase. The mixture was emulsified using a homomixer at a temperature of 70° C., and then cooled to prepare a foundation.

Ten testees were asked to use each of the foundations, and the testees evaluated the respective items of the sense of touch, good spreading, absence of stickiness, and good maintenance of make-up, in three grades (good: 2 points, medium: 1 point, poor: 0 point). This evaluation was considered as a sensory evaluation. Furthermore, the sensory evaluation results given by the respective testees were added up as a comprehensive evaluation (⊚: 15 points or more, ○: 10 to 14 points, △: 5 to 9 points, x: 4 points or less). The comprehensive evaluation results of the respective foundations are presented in Table 3.

TABLE 3

Blending amounts and evaluation results for foundations

| | | Blending amount (% by mass) | |
|---|---|---|---|
| | Name of blended component | Example 17 | Comparative Example 11 |
| A | Gelling agent of Example 1 | 3.00 | — |
| | Gelling agent of Comparative Example 9 | — | 3.00 |
| | Liquid paraffin | 4.00 | 4.00 |
| | Octyl palmitate *1 | 4.00 | 4.00 |
| | Decamethylcyclopentasiloxane (cyclic silicone) *2 | 3.00 | 3.00 |
| | Dimethylpolysiloxane 5 cs (non-volatile dimethylpolysiloxane) | 1.40 | 1.40 |
| | Dipentaerythrityl hexa(hydroxystearate/ stearate/rosinate) *3 | 1.00 | 1.00 |

TABLE 3-continued

Blending amounts and evaluation results for foundations

|   | Name of blended component | Blending amount (% by mass) Example 17 | Blending amount (% by mass) Comparative Example 11 |
|---|---|---|---|
|   | Polyether-modified silicone | 0.30 | 0.30 |
| B | Pigment base | 10.00 | 10.00 |
| C | Ion-exchanged water | 68.28 | 68.28 |
|   | Propylene glycol | 5.00 | 5.00 |
|   | Carboxyvinyl polymer | 0.01 | 0.01 |
|   | Methylparaben | 0.01 | 0.01 |
| Evaluation results | Sense of touch | ⊚ | ○ |
|   | Good spreading | ⊚ | Δ |
|   | Absence of stickiness | ⊚ | ○ |
|   | Good maintenance of make-up | ⊚ | ○ |

For the reference numerals *1 to *3 in Table 3, the following were used.
*1: SALACOS P-8 manufactured by Nisshin OilliO Group, Ltd.
*2: KF-995 manufactured by Shin-Etsu Chemical Co., Ltd.
*3: COSMOL 168ARV manufactured by Nisshin OilliO Group, Ltd.

As can be seen from Table 3, the foundation of Example 17 in which the gelling agent of Example 1 was incorporated was excellent in all of the items, compared to the foundation of Comparative Example 11 in which the gelling agent of Comparative Example 9 was incorporated.

(Evaluation of Cosmetic Preparation 2)

Example 1 and Comparative Example 9 were used to produce sunscreens of Example 18 and Comparative Example 12 by the following method, and an evaluation was performed.

The oily components A indicated in Table 4 were sufficiently stirred to prepare an oil phase, and the aqueous components B indicated in the same Table 4 were slowly added to the oil phase. The mixture was emulsified using a homomixer at a temperature of 70° C., and then cooled to prepare a sunscreen.

Ten testees were asked to use each of the sunscreens, and the testees evaluated the respective items of the sense of touch, good spreading, absence of stickiness, and fresh sensation, in three grades (good: 2 points, medium: 1 point, poor: 0 point). This evaluation was considered as a sensory evaluation. Furthermore, the sensory evaluation results given by the respective testees were added up as a comprehensive evaluation (⊚: 15 points or more, ○: 10 to 14 points, Δ: 5 to 9 points, x: 4 points or less). The comprehensive evaluation results of the respective sunscreens are presented in Table 4.

TABLE 4

Blending amounts and evaluation results for sunscreens

|   | Name of blended component | Blending amount (% by mass) Example 18 | Blending amount (% by mass) Comparative Example 12 |
|---|---|---|---|
| A | Gelling agent of Example 1 | 4.00 | — |
|   | Gelling agent of Comparative Example 9 | — | 4.00 |
|   | Octyl palmitate *1 | 15.00 | 15.00 |
|   | Liquid paraffin | 10.00 | 10.00 |
|   | Dimethylpolysiloxane 5 cs (non-volatile dimethylpolysiloxane) | 3.50 | 3.50 |
|   | Decamethylcyclopentasiloxane (cyclic silicone) *2 | 1.50 | 1.50 |
|   | Polyether-modified silicone | 1.50 | 1.50 |
|   | 2-Ethylhexyl paramethoxycinnamate *3 | 5.00 | 5.00 |

TABLE 4-continued

Blending amounts and evaluation results for sunscreens

|   | Name of blended component | Blending amount (% by mass) Example 18 | Blending amount (% by mass) Comparative Example 12 |
|---|---|---|---|
|   | Titanium dioxide | 5.00 | 5.00 |
|   | Zinc oxide | 5.00 | 5.00 |
| B | Ion-exchanged water | 45.99 | 45.99 |
|   | 1,3-Butylene glycol | 3.00 | 3.00 |
|   | Propylene glycol | 2.00 | 2.00 |
|   | Methylparaben | 0.01 | 0.01 |
| Evaluation results | Sense of touch | ⊚ | Δ |
|   | Good spreading | ⊚ | Δ |
|   | Absence of stickiness | ⊚ | ○ |
|   | Fresh sensation | ⊚ | ○ |

For the reference numerals *1 to *3 in Table 4, the following were used.
*1: SALACOS P-8 manufactured by Nisshin OilliO Group, Ltd.
*2: KF-995 manufactured by Shin-Etsu Chemical Co., Ltd.
*3: NOMCORT TAB manufactured by Nisshin OilliO Group, Ltd.

As can be seen from Table 4, the sunscreen of Example 18 in which the gelling agent of Example 1 was incorporated was excellent in all of the items, compared to the sunscreen of Comparative Example 12 in which the gelling agent of Comparative Example 9 was incorporated.

(Evaluation of Cosmetic Preparation 3)

Example 1 and Comparative Example 9 were used to produce lipsticks of Example 19 and Comparative Example 13 by the following method, and an evaluation was performed.

The components described in the following Table 5 were mixed, and then were heated to 120° C. to completely dissolve. Subsequently, the solution was removed of bubbles, introduced into a frame, and cooled. The product was taken out from the frame, and was set in a lipstick container.

Ten testees were asked to use each of the lipsticks, and the testees evaluated the respective items of the sense of touch, colorability, gloss, and maintenance of make-up of the lipstick, in three grades (good: 2 points, medium: 1 point, poor: 0 point). This evaluation was considered as a sensory evaluation. Furthermore, the sensory evaluation results given by the respective testees were added up as a comprehensive evaluation (⊚: 15 points or more, ○: 10 to 14 points, Δ: 5 to 9 points, x: 4 points or less).

The comprehensive evaluation results of the respective lipsticks are presented in Table 5.

TABLE 5

Blending amounts and evaluation results for lipsticks

| Name of blended component | Blending amount (% by mass) Example 19 | Blending amount (% by mass) Comparative Example 13 |
|---|---|---|
| Gelling agent of Example 1 | 6.00 | — |
| Gelling agent of Comparative Example 9 | — | 6.00 |
| Candelilla wax | 8.00 | 8.00 |
| Polyethylene wax | 6.00 | 6.00 |
| Diisostearyl malate *1 | 12.00 | 12.00 |
| Dipentaerythrityl hexa(hydroxystearate/stearate/rosinate) *2 | 10.00 | 10.00 |
| Glyceryl tri-2-ethylhexanoate *3 | 9.00 | 9.00 |
| Phenyltrimethicone | 7.00 | 7.00 |
| Octyl palmitate *4 | 6.00 | 6.00 |
| Liquid paraffin | 4.00 | 4.00 |
| Pigment base | 10.00 | 10.00 |
| Polyglyceryl-2 triisostearate *5 | 22.00 | 22.00 |

TABLE 5-continued

Blending amounts and evaluation results for lipsticks

|  |  | Blending amount (% by mass) | |
|---|---|---|---|
| Name of blended component | | Example 19 | Comparative Example 13 |
| Evaluation results | Sense of touch | ◎ | Δ |
| | Colorability | ◎ | ○ |
| | Gloss | ◎ | ○ |
| | Maintenance of make-up | ◎ | ○ |

For the reference numerals *1 to *5 in Table 5, the following were used.
*1: COSMOL 222 manufactured by Nisshin OilliO Group, Ltd.
*2: COSMOL 168ARV manufactured by Nisshin OilliO Group, Ltd.
*3: T.I.O. manufactured by Nisshin OilliO Group, Ltd.
*4: SALACOS P-8 manufactured by Nisshin OilliO Group, Ltd.
*5: COSMOL 43V manufactured by Nisshin OilliO Group, Ltd.

As can be seen from Table 5, the lipstick of Example 19 in which the gelling agent of Example 1 was incorporated, was excellent in all of the items, compared to the lipstick of Comparative Example 13 in which the gelling agent of comparative Example 9 was incorporated.

(Evaluation of Cosmetic Preparation 4)

Example 1 and Comparative Example 9 were used to produce cosmetic creams of Example 20 and Comparative Example 14 by the following method, and an evaluation was performed.

While sufficiently stirring the oily components A indicated in Table 6 at a temperature of 70° C., the aqueous components B indicated in the same Table 6, which had been heated to a temperature of 70° C., were slowly added thereto, and the mixture was emulsified using a homomixer, and then cooled to produce a cosmetic cream.

Ten testees were asked to use each of the cosmetic creams, and the testees evaluated the respective items of the sense of touch, good spreading, smoothness, and absence of stickiness of the cosmetic cream, in three grades (good: 2 points, medium: 1 point, poor: 0 point). This evaluation was considered as a sensory evaluation. Furthermore, the sensory evaluation results given by the respective testees were added up as a comprehensive evaluation (◎: 15 points or more, ○: 10 to 14 points, Δ: 5 to 9 points, x: 4 points or less). The comprehensive evaluation results of the respective cosmetic creams are presented in Table 6.

TABLE 6

Blending amounts and evaluation results for cosmetic creams

|  |  | Blending amount (% by mass) | |
|---|---|---|---|
| | Name of blended component | Example 20 | Comparative Example 14 |
| A | Gelling agent of Example 1 | 3.00 | — |
| | Gelling agent of Comparative Example 9 | — | 3.00 |
| | Polyether-modified silicone | 2.00 | 2.00 |
| | Liquid paraffin | 30.00 | 30.00 |
| | Octyl palmitate *1 | 15.00 | 15.00 |
| B | Ion-exchanged water | 47.99 | 47.99 |
| | Glycerin | 1.00 | 1.00 |
| | Propylene glycol | 1.00 | 1.00 |
| | Methylparaben | 0.01 | 0.01 |
| Evaluation results | Sense of touch | ◎ | ○ |
| | Good spreading | ◎ | Δ |
| | Smoothness | ◎ | ○ |
| | Ltd. Absence of stickiness | ◎ | ○ |

*1: SALACOS P-8 manufactured by Nisshin OilliO Group,

As can be seen from Table 6, the cosmetic cream of Example 20 in which the gelling agent of Example 1 was incorporated, was excellent in all of the items, compared to the cosmetic cream of Comparative Example 14 in which the gelling agent of Comparative Example 9 was incorporated.

(Evaluation of Cosmetic Preparation 5)

Example 1 was used to produce foundations (oily foundation) of Example 21 and Comparative Example 15 by the following method, and an evaluation was performed.

The oily components B indicated in Table 7 were sufficiently stirred at a temperature of 70° C., and the pigments A indicated in the same Table 7 were slowly added thereto. The mixture was emulsified using a homomixer, and then cooled to produce a foundation.

Ten testees were asked to use the foundations, and the testees evaluated the respective items of the sense of touch, good spreading, smoothness, and absence of stickiness of the foundation, in three grades (good: 2 points, medium: 1 point, poor: 0 point). This evaluation was considered as a sensory evaluation. Furthermore, the sensory evaluation results given by the respective testees were added up as a comprehensive evaluation (◎: 15 points or more, ○: 10 to 14 points, Δ: 5 to 9 points, x: 4 points or less). In addition, the produced foundations were stored in a constant temperature bath at 50° C., and after one month, the state of the foundations was checked to evaluate them in three grades (○: separation not observed, Δ: slight separation observed, x: complete separation). The comprehensive evaluation results of the respective foundations are presented in Table 7.

TABLE 7

Blending amounts and evaluation results for foundations (oily foundations)

|  |  | Blending amount (% by mass) | |
|---|---|---|---|
| | Name of blended component | Example 21 | Comparative Example 15 |
| A | Talc | 5.50 | 5.50 |
| | Titanium oxide | 40.00 | 40.00 |
| | Iron oxide black | 0.50 | 0.50 |
| | Iron oxide yellow | 3.50 | 3.50 |
| | Iron oxide red | 1.00 | 1.00 |
| B | Gelling agent of Example 1 | 4.50 | — |
| | Diisostearyl malate | 17.00 | 17.00 |
| | Dimethylpolysiloxane 10 cs (non-volatile dimethylpolysiloxane) | 5.00 | 5.00 |
| | Decamethylcyclopentasiloxane (cyclic silicone) | 23.00 | 27.50 |
| Evaluation results | Sense of touch | ◎ | ○ |
| | Good spreading | ◎ | Δ |
| | Smoothness | ◎ | ○ |
| | Absence of stickiness | ◎ | ○ |
| | State after storage at 50° C. for 1 month | ○ | Δ |

As can be seen from Table 7, the foundation of Example 21 in which the gelling agent of Example 1 was incorporated, was excellent in all of the items, compared to the foundation of Comparative Example 15.

(Evaluation of Cosmetic Preparation 6)

Example 1 was used to produce sunscreens (water-in-oil type emulsified sunscreen cream) of Example 22 and Comparative Example 16 by the following method, and an evaluation was performed.

While sufficiently stirring the oily components A indicated in Table 8 at a temperature of 70° C., pigment B was added thereto, and the mixture was taken as the oil phase portion.

The aqueous components C indicated in the same Table 8, which had been heated to a temperature of 70° C., were slowly added thereto, and the mixture was emulsified using a homomixer, and then cooled to produce a sunscreen.

Ten testees were asked to use the sunscreens, and the testees evaluated the respective items of the sense of touch, good spreading, smoothness, and absence of stickiness of the sunscreen, in three grades (good: 2 points, medium: 1 point, poor: 0 point). This evaluation was considered as a sensory evaluation. Furthermore, the sensory evaluation results given by the respective testees were added up as a comprehensive evaluation (⊚: 15 points or more, ○: 10 to 14 points, Δ: 5 to 9 points, x: 4 points or less). In addition, the produced sunscreens were stored in a constant temperature bath at 50° C., and after one month, the state of the sunscreens was checked to evaluate them in three grades (○: separation not observed, Δ: slight separation observed, x: complete separation). The comprehensive evaluation results of the respective sunscreens are presented in Table 8.

TABLE 8

Blending amounts and evaluation results for sunscreens (water-in-oil type emulsified sunscreen cream)

| | Name of blended component | Example 22 | Comparative Example 16 |
|---|---|---|---|
| A | Gelling agent of Example 1 | 3.00 | — |
| | Decamethylcyclopentasiloxane (cyclic silicone) | 13.50 | 13.50 |
| | Dimethylpolysiloxane 5 cs (non-volatile dimethylpolysiloxane) | 9.00 | 9.00 |
| | Diisostearyl malate | 4.50 | 4.50 |
| | Polyether-modified silicone | 3.00 | 3.00 |
| B | Titanium oxide | 10.00 | 10.00 |
| C | 1,3-Butylene glycol | 5.00 | 5.00 |
| | Sodium chloride | 1.00 | 1.00 |
| | Methylparaben | 0.20 | 0.20 |
| | Ion-exchanged water | 50.8 | 53.8 |
| Evaluation results | Sense of touch | ⊚ | ○ |
| | Good spreading | ⊚ | Δ |
| | Smoothness | ⊚ | ○ |
| | Absence of stickiness | ⊚ | ○ |
| | State after storage at 50° C. for 1 month | ○ | Δ |

As can be seen from Table 8, the sunscreen of Example 22 in which the gelling agent of Example 1 was incorporated, was excellent in all of the items, compared to the sunscreen of Comparative Example 16.

(Evaluation of Cosmetic Preparation 7)

Example 1 was used to produce cleansing products (cleansing oils) of Examples 23, 24 and 25, and Comparative Examples 17, 18 and 19 by the following method, and an evaluation was performed.

The components indicated in Table 9 were sufficiently stirred at a temperature of 70° C. to mix, and then the mixture was cooled to produce a cleansing product.

Ten testees were asked to use the cleansing products, and the testees evaluated the respective items of the sense of touch, good spreading, and absence of dripping of the cleansing product, in three grades (good: 2 points, medium: 1 point, poor: 0 point). This evaluation was considered as a sensory evaluation. Furthermore, the sensory evaluation results given by the respective testees were added up as a comprehensive evaluation (⊚: 15 points or more, ○: 10 to 14 points, Δ: 5 to 9 points, x: 4 points or less). The comprehensive evaluation results of the respective cleansing products are presented in Table 9.

TABLE 9

Blending amounts and evaluation results for cleansing products (cleansing oils)

| Name of blended component | Example 23 | Example 24 | Example 25 | Comparative Example 17 | Comparative Example 18 | Comparative Example 19 |
|---|---|---|---|---|---|---|
| Polyoxyethylene sorbite tetraoleate | 16.0 | — | — | 16.0 | — | — |
| Decaglyceryl monooleate | — | 10.5 | — | — | 10.5 | — |
| Diglyceryl monooleate | — | 4.5 | — | — | 4.5 | — |
| Decaglyceryl dioleate | — | — | 14.0 | — | — | 14.0 |
| Diglyceryl sesquicaprylate | — | — | 6.0 | — | — | 6.0 |
| Ethylhexyl palmitate | 79.0 | 80.0 | — | 84.0 | 85.0 | — |
| Cetyl 2-ethylhexanoate | — | — | 75.0 | — | — | 80.0 |
| Gelling agent of Example 1 | 5.0 | 5.0 | 5.0 | — | — | — |
| Sense of touch | ⊚ | ⊚ | ⊚ | ○ | ○ | ○ |
| Good spreading | ⊚ | ⊚ | ⊚ | Δ | Δ | Δ |
| Absence of dripping | ⊚ | ⊚ | ⊚ | Δ | Δ | Δ |

As can be seen from Table 9, the cleansing products of Examples 23, 24 and 25 in which the gelling agent of Example 1 was incorporated, were excellent in all of the items compared to the cleansing products of Comparative Examples 17, 18 and 19.

(Evaluation of Solubility in Non-Volatile Dimethylpolysiloxane and Gelation)

A mixture of 1.0 g of the gelling agent of Example 1 and 19.0 g of an oil agent, a mixture of 6.0 g of the gelling agent of Example 1 and 14.0 g of an oil agent, and a mixture of 1.0 g of the gelling agent of Comparative Example 9 and 19.0 g of an oil agent were heated to 80° C., so that the gelling agent of Example 1 or Comparative Example 9 was completely dissolved in the oil agent. While maintaining these mixtures at 80° C., dimethylpolysiloxane 10 cs (non-volatile dimethylpolysiloxane) was added in portions of 0.1 g each, and the time point at which the mixture began to become turbid was determined as the completion point. The results of the mass of addition of dimethylpolysiloxane 10 cs (non-volatile dimethylpolysiloxane) with respect to the total mass of the gelling agent of Example 1 or Comparative Example 9 and the oil agent, expressed in %, at this time point where the mixture began to become turbid, are presented in Table 10.

agent, and then cooled to produce a gelation product containing the gelling agent of Example 1. The gelation product was said to have thixotropic properties if, when the bottle was shaken to mix, the gelation product turned into a sol, and when the sol product was left to stand for 30 minutes and then the bottle was inverted, the content did not begin to flow.

TABLE 11

Evaluation of thixotropic properties

| Subject oil agent | Concentration of gelling agent of Example 1 | Presence or absence of thixotropic properties |
|---|---|---|
| Liquid paraffin | 6~10% | ○ |
| Glyceryl tri-2-ethylhexanoate *1 | 5~10% | ○ |
| Octyl palmitate *2 | 7~10% | ○ |
| Cetyl octanoate *3 | 7~10% | ○ |
| Dicapryl carbonate | 8~13% | ○ |

For the reference numerals *1 to *3 in Table 11, the following were used.
*1: T.I.O. manufactured by Nisshin OilliO Group, Ltd.
*2: SALACOS P-8 manufactured by Nisshin OilliO Group, Ltd.
*3: SALACOS 816T manufactured by Nisshin OilliO Group, Ltd.

TABLE 10

| Subject oil agent | Example 26 Mixture of 1.0 g of gelling agent of Example 1 and 19.0 g of oil agent | Example 27 Mixture of 6.0 g of gelling agent of Example 1 and 14.0 g of oil agent | Comparative Example 20 Mixture of 1.0 g of gelling agent of Comparative Example 9 and 19.0 g of oil agent |
|---|---|---|---|
| Isononyl isononanoate *1 | 200% or more | 187% | 108% |
| Isotridecyl isononanoate *2 | 200% or more | 187% | 100% |
| Neopentyl glycol didecanoate *3 | 200% or more | 150% | 120% |
| Pentaerythrityl tetraoctanoate *4 | 200% or more | 138% | 76% |
| Erythrityl triethylhexanoate *5 | 200% or more | 131% | 90% |
| Liquid paraffin (70 sec) | 200% or more | 157% | 74% |

As can be seen from the results of Table 10, the dissolution ability of dimethylpolysiloxane 10 cs (non-volatile dimethylpolysiloxane) on the gelling agent of Example 1 was excellent, compared to that on the gelling agent of Comparative Example 9. That is, it was understood that the solubility in a non-volatile dimethylpolysiloxane was good. Furthermore, the mixtures obtained by adding dimethylpolysiloxane 10 cs (non-volatile dimethylpolysiloxane) to the mixture of 6.0 g of the gelling agent of Example 1 and 14.0 g of an oil agent, in the amount of the values of Example 27 in Table 10, all dissolved under heating at 80° C., and gelled after cooling.

(Evaluation of Thixotropic Properties)

The gelling agent of Example 1 and an oil agent were mixed, and an evaluation of whether the mixture would exhibit thixotropic properties or not, was performed. The type of the oil agent and the blending amount of the gelling agent of Example 1 are presented in Table 11. In regard to the method for evaluation of thixotropic properties, 50 g of a mixture in which the gelling agent of Example 1 was blended with the oil agent at the proportions indicated in Table 11 was produced in a bottle having a capacity of 100 ml, and the mixture was heated to 80° C. to uniformly dissolve the gelling It was confirmed that thixotropic properties were imparted by incorporating the gelling agent of Example 1 to the oil agents indicated in Table 11 at the respective concentrations indicated in percentage by mass.

(Evaluation of Cosmetic Preparation 8)

Example 1, or glyceryl behenate/eicosanedioate or dextrin palmitate, both of which are well known oil gelling agents, was used individually or used in combination, to produce cleansing products of Examples 28 to 35 and Comparative Examples 21 to 24 by the following method, and an evaluation was performed.

The components indicated in Table 12 were sufficiently stirred and mixed at a temperature of 90° C., and then cooled to produce a cleansing product.

Ten testees were asked to use the cleansing products, and the testees evaluated the respective items of the sense of touch, smoothness, and ease of use of the cleansing product, in three grades (good: 2 points, medium: 1 point, poor: 0 point). This evaluation was considered as a sensory evaluation. Furthermore, the sensory evaluation results given by the respective testees were added up as a comprehensive evaluation (⊚: 15 points or more, ○: 10 to 14 points, Δ: 5 to 9 points, ×: 4 points or less). The comprehensive evaluation results of the respective cleansing products are presented in Table 12.

TABLE 12

Blending amounts and evaluation results for cleansing products

| Name of blended component | Blending amount (% by mass) | | | | | | | | | | | |
|---|---|---|---|---|---|---|---|---|---|---|---|---|
| | Example | | | | | | | | Comparative Example | | | |
| | 28 | 29 | 30 | 31 | 32 | 33 | 34 | 35 | 21 | 22 | 23 | 24 |
| Polyoxyethylene sorbite tetraoleate | 16.0 | 16.0 | — | — | — | — | — | — | 16.0 | — | — | — |
| Polyoxyethylene glyceryl triisostearate | — | — | 8.0 | 8.0 | — | — | — | — | — | 8.0 | — | — |
| Polyoxyethylene glyceryl isostearate | — | — | 8.0 | 8.0 | — | — | — | — | — | 8.0 | — | — |
| Decaglyceryl monooleate | — | — | — | — | 10.5 | 10.5 | — | — | — | — | 10.5 | — |
| Diglyceryl monooleate | — | — | — | — | 4.5 | 4.5 | — | — | — | — | 4.5 | — |
| Decaglyceryl dioleate | — | — | — | — | — | — | 14.0 | 14.0 | — | — | — | 14.0 |
| Diglyceryl sesquicaprylate | — | — | — | — | — | — | 6.0 | 6.0 | — | — | — | 6.0 |
| Liquid paraffin | 74.0 | 76.0 | 74.0 | 76.0 | 75.0 | 77.0 | 40.0 | 40.0 | 74.0 | 74.0 | 75.0 | 40.0 |
| Cetyl 2-ethylhexanoate | — | — | — | — | — | — | 30.0 | 30.0 | — | — | — | 30.0 |
| Glyceryl behenate/eicosanedioate (*1) | — | 3.0 | — | 3.0 | — | 3.0 | — | — | 10.0 | 10.0 | 10.0 | — |
| Dextrin palmitate | — | — | — | — | — | — | — | 5.0 | — | — | — | 10.0 |
| Gelling agent of Example 1 | 10.0 | 5.0 | 10.0 | 5.0 | 10.0 | 5.0 | 10.0 | 5.0 | — | — | — | — |
| Sense of touch | ◉ | ◉ | ◉ | ◉ | ◉ | ◉ | ◉ | ◉ | x | x | x | Δ |
| Smoothness | ◉ | ◉ | ◉ | ◉ | ◉ | ◉ | ◉ | ◉ | Δ | Δ | Δ | Δ |
| Ease of use | ◉ | ◉ | ◉ | ◉ | ◉ | ◉ | ◉ | ◉ | Δ | Δ | Δ | Δ |

*1: NOMCORT HK-G manufactured by Nisshin OilliO Group, Ltd.

As can be seen from Table 12, the cleansing products of Examples 28 to 35 in which the gelling agent of Example 1 and other oil gelling agents were incorporated, were excellent in all of the items compared to the cleansing products of Comparative Examples 21 to 24.

(Evaluation of Cosmetic Preparation 9)

Example 1 was used to produce lip glosses of Examples 36 to 39 and Comparative Examples 25 and 26 by the following method, and an evaluation was performed.

The components indicated in Table 13 were sufficiently stirred and mixed at a temperature of 90° C., and then cooled to produce a lip gloss.

Ten testees were asked to use the lip glosses, and the testees evaluated the respective items of the sense of touch and good spreading of the lip gloss, in three grades (good: 2 points, medium: 1 point, poor: 0 point). This evaluation was considered as a sensory evaluation. Furthermore, the sensory evaluation results given by the respective testees were added up as a comprehensive evaluation (◉: 15 points or more, ○: 10 to 14 points, Δ: 5 to 9 points, x: 4 points or less). The comprehensive evaluation results of the respective lip glosses are presented in Table 13.

TABLE 13

Blending amounts and evaluation results for lip glosses

| Name of blended component | Blending amount (% by mass) | | | | | |
|---|---|---|---|---|---|---|
| | Example 36 | Example 37 | Example 38 | Example 39 | Comparative Example 25 | Comparative Example 26 |
| Hydrogenated polyisobutene | 53.0 | 53.0 | 53.0 | 53.0 | 53.0 | 53.0 |
| Diisostearyl malate | 20.0 | 20.0 | 20.0 | 20.0 | 20.0 | 20.0 |
| Pentaerythrityl tetraethylhexanoate | 5.0 | 5.0 | 5.0 | 5.0 | 5.0 | 5.0 |
| Cetyl ethylhexanoate | 4.0 | 4.0 | 4.0 | 4.0 | 4.0 | 4.0 |

TABLE 13-continued

Blending amounts and evaluation results for lip glosses

| Name of blended component | Blending amount (% by mass) | | | | | |
|---|---|---|---|---|---|---|
| | Example 36 | Example 37 | Example 38 | Example 39 | Comparative Example 25 | Comparative Example 26 |
| Polyglyceryl-2 triisostearate | 3.5 | 3.5 | 3.5 | 3.5 | 3.5 | 3.5 |
| Neopentyl glycol dicaprylate | 3.0 | 3.0 | 3.0 | 3.0 | 3.0 | 3.0 |
| Pentaerythrityl tetraisostearate | 2.5 | 2.5 | 2.5 | 2.5 | 2.5 | 2.5 |
| Silica | 3.0 | 3.0 | 3.0 | 3.0 | 3.0 | 3.0 |
| Mica | 1.0 | 1.0 | 1.0 | 1.0 | 1.0 | 1.0 |
| Iron oxide | 0.5 | 0.5 | 0.5 | 0.5 | 0.5 | 0.5 |
| Titanium oxide | 0.3 | 0.3 | 0.3 | 0.3 | 0.3 | 0.3 |
| Tocopherol | 0.1 | 0.1 | 0.1 | 0.1 | 0.1 | 0.1 |
| Fragrance | 0.1 | 0.1 | 0.1 | 0.1 | 0.1 | 0.1 |
| Glyceryl behenate/eicosanedioate (*1) | — | 2.0 | — | — | 4.0 | — |
| Dextrin palmitate | — | — | 2.0 | — | — | — |
| Ceresin | — | — | — | 2.0 | — | 4.0 |
| Gelling agent of Example 1 | 4.0 | 2.0 | 2.0 | 2.0 | — | — |
| Sense of touch | ◎ | ◎ | ◎ | ○ | x | Δ |
| Good spreading | ◎ | ◎ | ◎ | ◎ | Δ | Δ |

*1: NOMCORT HK-G manufactured by Nisshin OilliO Group, Ltd.

As can be seen from Table 13, the lip glosses of Examples 36 to 39 in which the gelling agent of Example 1 was incorporated, were excellent in all of the items compared to the lip glosses of Comparative Examples 25 and 26.

(Production of Cosmetic Preparation 10)

Example 1 was used to produce a hair cream of Example 40 by the following method.

The oily components A indicated in Table 14 are adjusted to 80° C., while sufficiently stirring them. The aqueous components B indicated in the same table are adjusted to 80° C., while sufficiently stirring them. While stirring, the oily components A were added to the aqueous components B, and the mixture was emulsified using a homomixer, and then cooled to prepare a hair cream.

TABLE 14

Blending amounts for hair cream

| | Name of blended component | Blending amount (% by mass) Example 40 |
|---|---|---|
| A | Gelling agent of Example 1 | 4.00 |
| | Liquid paraffin | 20.00 |
| | Octyldodecanol | 7.50 |
| | Beeswax | 2.00 |
| | Petrolatum | 2.00 |
| | Stearic acid | 0.50 |
| | Sorbitan sesquioleate *1 | 2.00 |
| | Sorbitan sesquiisostearate *2 | 1.00 |
| | Cetanol | 1.00 |
| B | Ion-exchanged water | 55.65 |
| | Glycerin | 4.00 |
| | Carboxyvinyl polymer | 0.10 |
| | Xanthan gum | 0.10 |
| | Edetic acid salt | 0.05 |
| | Sodium chloride | 0.05 |
| | Methylparaben | 0.05 |

For the reference numerals *1 to *2 in Table 14, the following were used.
*1: COSMOL 82 manufactured by Nisshin OilliO Group, Ltd.
*2: COSMOL 182V manufactured by Nisshin OilliO Group, Ltd.

(Production of Cosmetic Preparation 11)

Example 1 was used to produce a hair wax of Example 41 by the following method.

The oily components A indicated in Table 15 were sufficiently stirred at a temperature of 80° C., and then cooled to obtain a hair wax.

TABLE 15

Blending amounts for hair wax

| | Name of blended component | Blending amount (% by mass) Example 41 |
|---|---|---|
| A | Gelling agent of Example 1 | 10.00 |
| | Diisostearyl malate *1 | 55.00 |
| | Castor oil | 20.00 |
| | Olive oil | 10.00 |
| | Beeswax | 2.00 |
| | Wood wax | 2.00 |
| | Glyceryl (behenate/eicosanedioate) *2 | 0.50 |
| | Polyglyceryl-10 (behenate/eicosanedioate) *3 | 0.50 |

For the reference numerals *1 to *3 in Table 15, the following were used.
*1: COSMOL 222 manufactured by Nisshin OilliO Group, Ltd.
*2: NOMCORT HK-G manufactured by Nisshin OilliO Group, Ltd.
*3: NOMCORT HK-P manufactured by Nisshin OilliO Group, Ltd.

(Production of Cosmetic Preparation 12)

Example 1 was used to produce a hair rinse of Example 42 by the following method, and an evaluation was performed.

The components A indicated in Table 16 are sufficiently stirred at a temperature of 70° C. The components B were sufficiently stirred at a temperature of 70° C., and then the components A at 70° C. were added thereto. The mixture was emulsified using a homomixer, and then cooled to obtain a hair rinse.

TABLE 16

Blending amounts for hair rinse

| | Name of blended component | Blending amount (% by mass) Example 42 |
|---|---|---|
| A | Gelling agent of Example 1 | 0.50 |
| | Dimethylpolysiloxane 1000 cs (non-volatile dimethylpolysiloxane) | 1.00 |
| | Liquid paraffin | 1.00 |
| | Stearyl alcohol | 0.50 |
| | Amino-modified silicone | 0.50 |
| | Polyoxyethylene stearyl ether | 0.50 |
| | Polyglyceryl-2 monoisostearate *1 | 0.50 |
| | Polyglyceryl-2 diisostearate *2 | 0.25 |
| | Sorbitan sesquioleate *3 | 0.25 |

TABLE 16-continued

Blending amounts for hair rinse

| | Name of blended component | Blending amount (% by mass) Example 42 |
|---|---|---|
| B | Cetyltrimethylammonium chloride | 4.00 |
| | Glycerin | 0.90 |
| | Ion-exchanged water | 90.00 |
| | Methylparaben | 0.10 |

For the reference numerals *1 to *3 in Table 16, the following were used.
*1: COSMOL 41V manufactured by Nisshin OilliO Group, Ltd.
*2: COSMOL 42V manufactured by Nisshin OilliO Group, Ltd.
*3: COSMOL 82 manufactured by Nisshin OilliO Group, Ltd.

The invention claimed is:

1. An esterification reaction product having a hydroxyl value of 30 or less, the esterification reaction product being obtainable by subjecting the following component A, component B, component C and component D to an esterification reaction, wherein the blending ratio of the component A and the component B at the time of the esterification reaction is such that component A:component B=1.0 mole:0.10 to 0.20 moles:
   component A: a polyhydric alcohol or a condensate thereof,
   component B: a saturated dibasic acid having 10 to 28 carbon atoms,
   component C: a linear saturated fatty acid having 16 to 28 carbon atoms, and
   component D: a branched saturated fatty acid having 8 to 28 carbon atoms.

2. The esterification reaction product according to claim 1, wherein the blending ratios of the respective components at the time of the esterification reaction are such that component A:component C=1.0 mole:1.0 to 7.5 moles, and component A:component D=1.0 mole:0.2 to 2.3 moles.

3. The esterification reaction product according to claim 1, wherein the component A is selected from the group consisting of glycerin, trimethylolpropane, pentaerythritol, diglycerin and decaglycerin.

4. The esterification reaction product according to claim 1, wherein the component B is selected from the group consisting of eicosanedioic acid, octadecanedioic acid and sebacic acid.

5. The esterification reaction product according to claim 1, wherein the component C is selected from the group consisting of palmitic acid, stearic acid and behenic acid.

6. The esterification reaction product according to claim 1, wherein the component D is isooctylic acid or isostearic acid.

7. A gelling agent comprising the esterification reaction product according to claim 1.

8. A thixotropy imparting agent comprising the esterification reaction product according to claim 1.

9. A cosmetic preparation comprising the esterification reaction product according to claim 1.

10. The cosmetic preparation according to claim 9, comprising a cyclic silicone or a volatile dimethylpolysiloxane, and/or an oil agent.

11. The cosmetic preparation according to claim 9, comprising a non-volatile dimethylpolysiloxane and an oil agent.

12. The cosmetic preparation according to claim 9, wherein the cosmetic preparation is an oily cosmetic preparation or a water-in-oil type emulsified cosmetic preparation.

13. The cosmetic preparation according to claim 9, wherein the cosmetic preparation is selected from the group consisting of a lipstick, a cream, an emulsion, a foundation, a sunscreen, and a cleansing product.

14. The esterification reaction product according to claim 2, wherein the component A is selected from the group consisting of glycerin, trimethylolpropane, pentaerythritol, diglycerin and decaglycerin.

15. The esterification reaction product according to claim 2, wherein the component B is selected from the group consisting of eicosanedioic acid, octadecanedioic acid and sebacic acid.

16. The esterification reaction product according to claim 3, wherein the component B is selected from the group consisting of eicosanedioic acid, octadecanedioic acid and sebacic acid.

17. The esterification reaction product according to claim 2, wherein the component C is selected from the group consisting of palmitic acid, stearic acid and behenic acid.

18. The esterification reaction product according to claim 3, wherein the component C is selected from the group consisting of palmitic acid, stearic acid and behenic acid.

19. The esterification reaction product according to claim 4, wherein the component C is selected from the group consisting of palmitic acid, stearic acid and behenic acid.

20. The esterification reaction product according to claim 2, wherein the component D is isooctylic acid or isostearic acid.

\* \* \* \* \*